(12) United States Patent
Wiesel (10) Patent No.: US 6,519,490 B1
(45) Date of Patent: Feb. 11, 2003

(54) METHOD OF AND APPARATUS FOR DETECTING ARRHYTHMIA AND FIBRILLATION

(76) Inventor: Joseph Wiesel, 484 Duryea Ter., West Hempstead, NY (US) 11552

( * ) Notice: Subject to any disclaimer, the term of this patent is extended or adjusted under 35 U.S.C. 154(b) by 0 days.

(21) Appl. No.: 09/467,233

(22) Filed: Dec. 20, 1999

(51) Int. Cl.[7] ................................................. A61B 5/04
(52) U.S. Cl. ........................................................ 600/518
(58) Field of Search .................................. 600/382, 384, 600/485, 500, 502, 504, 509, 513, 515, 516, 517, 518, 519, 521, 526; 607/4, 5, 6, 14, 18, 25

(56) References Cited

U.S. PATENT DOCUMENTS

| | | | |
|---|---|---|---|
| 4,260,951 A | * 4/1981 | Lewyn | 328/165 |
| 4,621,643 A | 11/1986 | New, Jr. et al. | |
| 4,685,464 A | 8/1987 | Goldberger et al. | |
| 4,700,708 A | 10/1987 | New, Jr. et al. | |
| 5,113,869 A | 5/1992 | Nappholz et al. | |
| 5,117,834 A | 6/1992 | Kroll et al. | |
| 5,228,449 A | * 7/1993 | Christ et al. | 128/691 |
| 5,342,404 A | * 8/1994 | Alt et al. | 607/6 |
| 5,456,261 A | 10/1995 | Luczyk | |
| 5,471,991 A | 12/1995 | Shinnar | |
| 5,609,158 A | 3/1997 | Chan | |
| 5,626,143 A | 5/1997 | Meyer, III | |
| 5,772,604 A | 6/1998 | Langberg et al. | |
| 5,842,997 A | 12/1998 | Verrier et al. | |
| 5,941,831 A | 8/1999 | Turcott | |
| 6,249,700 B1 | * 6/2001 | Alt | 607/4 |
| 6,327,499 B1 | * 12/2001 | Alt | 607/4 |

* cited by examiner

*Primary Examiner*—Jeffrey R. Jastrzab
*Assistant Examiner*—Frances P. Oropeza
(74) *Attorney, Agent, or Firm*—Gibbons, Del Deo, Dolan, Griffinger & Vecchione (57) ABSTRACT

The presence of irregular heartbeat and/or possible atrial fibrillation is determined by analyzing a measured pulse rate pattern or heart rate pattern. The standard deviation and mean of time intervals each corresponding to a respective heartbeat are determined and compared to a threshold value. When quotient formed by dividing the standard deviation by the mean has a value greater than or equal to the threshold value, the shortest one of the time intervals and its succeeding time intervals are determined, and the succeeding time interval is compared to the mean. If the succeeding time interval is less than the mean, then the heartbeat is irregular. Alternatively, if the succeeding time interval is greater than the mean, the shortest time interval and its succeeding time interval are eliminated from the sample values, a new mean and standard deviation are determined, and the quotient of the new standard deviation divided by the new mean are compared to the threshold value. When the quotient is greater than the threshold value, the next shortest interval is determined, and the absolute value of the difference between the next shortest interval and the shortest interval is compared to an empirically determined value. If the difference is greater than the empirically determined value, the heartbeat is irregular. Alternatively, if the difference is greater than the empirically determined value, then the next shortest interval and its succeeding interval are redefined as the new shortest interval and is succeeding interval. The steps are repeated until it is determined that the heartbeat is regular or irregular.

40 Claims, 4 Drawing Sheets

METHOD OF AND APPARATUS FOR DETECTING ARRHYTHMIA AND FIBRILLATION

CROSS-REFERENCE TO RELATED PATENT APPLICATIONS

None

STATEMENT REGARDING FEDERALLY SPONSORED RESEARCH OR DEVELOPMENT

None

BACKGROUND OF THE INVENTION

1. Field of the Invention

The present invention generally relates to a method of and an apparatus for detecting irregular heartbeats and, more particularly, to monitoring and analyzing pulse rates for detecting possible atrial fibrillation.

2. Discussion of the Related Art

The heart is the major muscle that functions as the primary pump for blood flow throughout the body. The heart contains two upper chambers called atria and two lower chambers called ventricles. The right atrium receives oxygen-depleted blood while the left atrium receives blood enriched with oxygen from the lungs. When the atria are full, the outlet valves within the heart open and the atria squeeze blood into the ventricles. The right ventricle then pumps oxygen-depleted blood to the lungs while the left ventricle pumps oxygen-enriched blood to all parts of the body. In this fashion, the heart functions primarily as a double sided pump.

The heart's internal pacemaker, known as the sinus node, signals the start of each heart beat. This signal originates in the right atrium in the sinoatrial node and travels simultaneously to the left atrium and down to the interatrial septum to the atrioventricular node. The cycle of electrical stimulation that normally occurs is referred to as normal sinus rhythm.

When a rhythm abnormality is present, however, there may exist an abnormal condition known as fibrillation. Fibrillation may occur as a result of an abnormality with either the ventricle and/or the atria. Atrial fibrillation is an abnormal heart condition in which the atria of the heart provide irregular impulses to the atrioventricular node so that an irregular heartbeat results.

Atrial fibrillation is one of the most common arrhythmias requiring medical attention. Atrial fibrillation may be caused by a number of heart conditions, such as angina, myocardial infarction, heart valve abnormalities, and high blood pressure. These conditions may stretch or scar the atria, thereby causing irregularities in the heart system. Atrial fibrillation may also accompany lung problems or thyroid gland disorders and is also associated with significant morbidity and possible mortality. All persons, young and old, female or male, including the visually and/or sight impaired, may experience atrial fibrillation.

Atrial fibrillation may occur intermittently or chronically. The most serious complication of atrial fibrillation is formation of a blood clot in the left atrium which may result in a stroke. Many people who develop atrial fibrillation, however, are unaware of their abnormal rhythm, Some in the medical profession have, therefore, advocated self screening of the pulse rate to detect for the possible occurrence of atrial fibrillation. The literature, however, is generally limited to disclosing instructions for manually taking one's pulse rate accompanied with additional descriptive information.

The reason for taking the pulse rate to detect atrial fibrillation is that the pulse rate corresponds to the heart rate. The pumping action of the heart displaces blood in the rest of the body. The pulse is the movement of blood caused by the heart's pumping, and the pulse rate is the number of times that the blood is displaced during a fixed period, conventionally an interval of one minute.

Because of the correspondence between the heartbeat rate and pulse rate, atrial fibrillation causes an irregular detected pulse wherever a pulse can be palpated. Normal sinus rhythm produces a heartbeat of a fixed number of beats per minute with equal interval between beats. Fibrillation is detected when the time between the beats is irregular, that is the time between beats changes irregularly.

There are several devices available that measure both blood pressure and pulse rate, but none of these devices is capable of monitoring, detecting and/or communicating whether or not an irregular heartbeat is present to indicate possible atrial fibrillation. The commercially available devices measure the number of pulse beats over a preset time interval, usually ten (10) seconds, but these devices neither analyze nor determine the presence of irregular heartbeat rhythms.

Commercially available devices for determining pulse rates use several methods including: i) measuring a pulse beat when systolic pressure peaks are detected such as by using an inflated cuff that is wrapped around the upper arm, ii) utilizing electrodes to determine pulse rates in the same manner used while taking an EKG, and iii) detecting pulse beats from changes in light transmission through body appendages, such as through the fingers, where a pulse is recorded whenever the difference in the amount of light absorbed between one point of the appendage and another point on the appendage changes. The change in transmission results from the pulse moveably changing the volume of blood flowing through the appendage which changes, in turn, the amount of light absorbed in the appendage.

What is needed is a method and apparatus to detect the pulse beats during a certain interval of time.

What is needed is a method and apparatus to detect the presence of irregular heartbeats and communicate this condition to the user so that the user is alerted to consult a medical practitioner for further testing and/or treatment.

What is also needed is a method that can differentiate an irregular pulse rate pattern from a normal pulse rate pattern and from common heart rhythm patterns that are not of significant risk, such as regular sinus rhythm, sinus arrhythmia, atrial premature beats and ventricular premature beats.

What also is a needed is a home monitoring method and apparatus that analyzes pulse rates for the presence of irregular pulse rhythms and that communicates this information to the user.

What further is needed is a method of and an apparatus for detecting irregular pulse rhythms during a time period and storing this information so that comparisons may be made with the pulse rate rhythms at later times.

What is further needed is a noninvasive and relatively simple method and apparatus that monitors pulse rate irregularities to detect fibrillations, including the possibility of atrial fibrillation, and that is suitable for use of all ages, and by the hearing and/or visually impaired and that is relatively easy to use.

What is still further needed is a monitoring method and apparatus that detects the presence of irregular heartbeats and then displays and stores: i) the number of irregular pulse beats during a pre-selected time interval; and ii) the duration of time between beats during selected intervals.

Yet another need is for a monitoring method and apparatus that determine whether or not a heartbeat is irregular based on algorithmic or heuristic operations performed on selected pulse rate or heartbeat data.

BRIEF SUMMARY OF THE INVENTION

The present invention provides a method and apparatus that (i) detects the presence of irregular heartbeats by analyzing a pulse rate pattern, that is, by analyzing the pulse beat rhythm during a time interval; (ii) determines whether this pulse rate pattern indicates a possible atrial fibrillation or other irregularity; and then (iii) communicates this information to the user so that a medical practitioner may be consulted for further testing and/or treatment. The present invention also provides a method of and an apparatus for detecting irregular pulse rhythms during a time period and storing this information for comparison with the pulse rate rhythm at later time periods. The present invention may also detect irregular pulse rhythms over multiple time periods and capture the similarities and/or differences in the pulse rate for selected intervals over various time periods.

The present invention further provides a noninvasive method of and an apparatus for monitoring pulse rate irregularities to detect atrial fibrillation. The invention may store and display information such as the number of irregular pulse beats during pre-selected time intervals and the duration of time between beats during the selected intervals. The invention also determines the presence of an irregular heartbeat via algorithmic or heuristic operations performed on the relevant data.

For patients with a baseline rhythm abnormality, or for those who want improved accuracy for detecting atrial fibrillation, a device comprised of electrodes may be placed on the skin. This device uses the actual electrocardiogram, in contrast to the pulse, to determine whether an atrial fibrillation warning should be indicated. The electrodes may be wrist straps that are placed on the arms or which are removably secured to various areas on the torso, arms or legs. This device may be used in conjunction with an electrocardiogram (EKG) recording device. The device may record the electrocardiogram, analyze the heartbeats, and display the appropriate warnings when pre-selected criteria for fibrillation are met. The present invention also works using either the heartbeat rate or the pulse rate.

Pulse rates may also be monitored by tracking the systolic peak that coincides with each heartbeat. Typically, an inflatable cuff is wrapped around the upper arm of a person and is inflated to a pressure greater than the person's blood pressure. Each heartbeat causes a rise in the blood pressure up to a systolic peak which corresponds to a pulse beat.

Pulse rates may also be monitored through changes in light transmitted through various body appendages. Each pulse beat changes the light transmission through a location on the appendage. The change in the light transmission over a time interval yields a pulse rate or an average pulse rate.

A monitoring method of the present invention includes detecting irregular pulse beats, analyzing the irregularity based on one or more predetermined factors, and communicating this information to a user such as via a screen display, a paper printout, a tone, or auditory, vibratory or other sensory communication.

In a preferred embodiment, the invention utilizes algorithmic or heuristic techniques to determine whether the irregular pulse beat(s) signals the possible presence of atrial fibriallation.

The present invention is also directed to an apparatus for performing the above-described methods.

Other features and advantages of the present invention will become apparent from the following detailed description of the invention with reference to the accompanying drawings.

BRIEF DESCRIPTION OF THE DRAWINGS

The invention will now be described in greater detail in the following detailed description with the reference to the drawings in which.

DETAILED DESCRIPTION OF THE INVENTION

Figure 1:
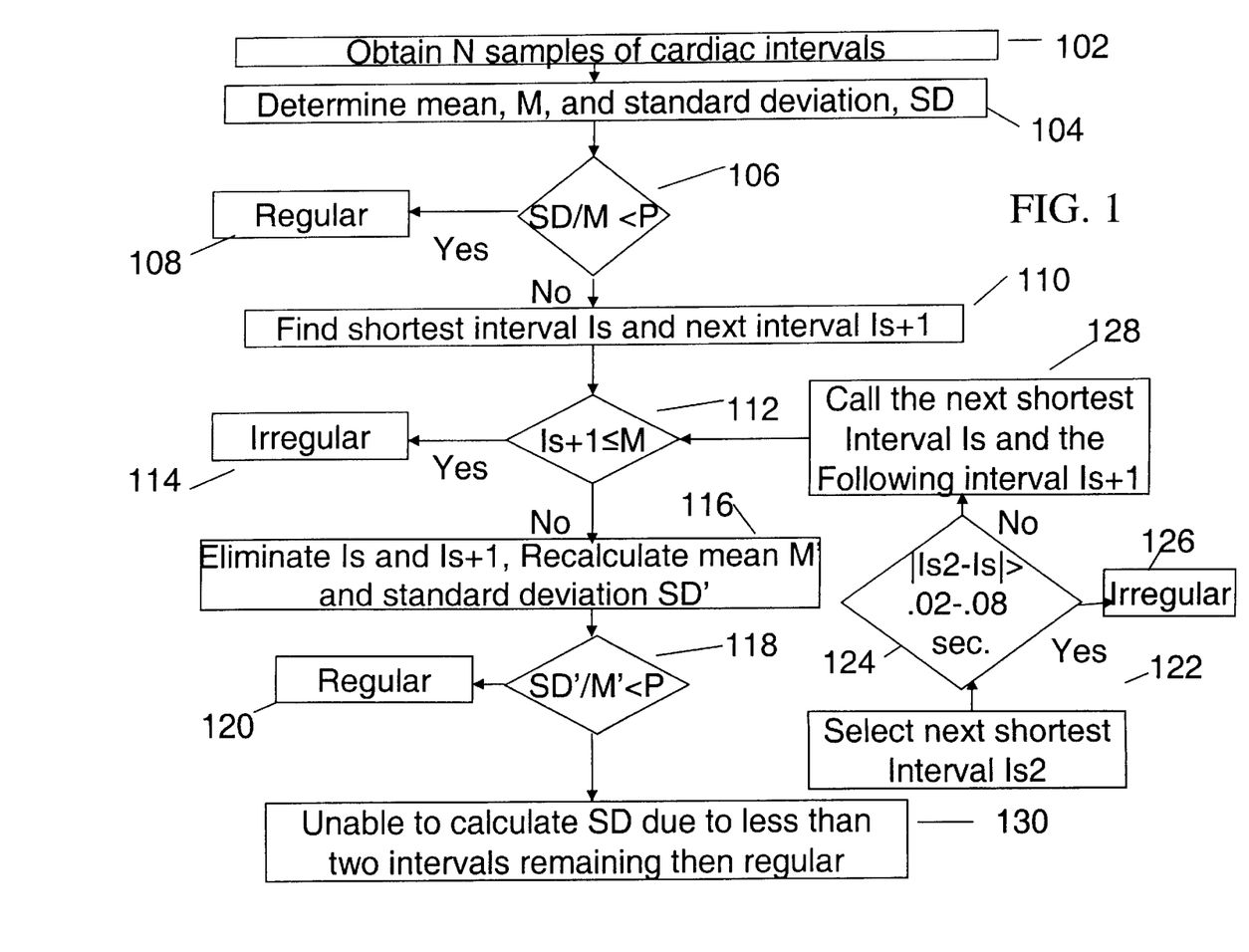
FIG. 1 is a flow chart depicting the various steps of the method for detection of possible atrial fibrillation in accordance with the invention.

FIG. 1 illustrates a preferred method for analyzing pulse beat patterns for the detection of atrial fibrillation by comparing the standard deviation for a fixed number of intervals. Initially, N samples are taken by measuring the pulse rate over N intervals, as step 102 shows. Then, as shown at step 104, the mean value M and the standard deviation SD of the N sample values are calculated.

In the vast majority of people with regular sinus rhythm or sinus arrhythmia, the standard deviation for a fixed number of intervals N is less than or equal to a, fixed percentage of the mean, P which has been shown to be about in the range of 0.05–0.10 with 0.07 being the preferred value of P. As step 106 shows, when the ratio of SD/M is less than P, the heart rhythm is regular, as step 108 shows. If the ratio is greater than or equal to P, further analysis is needed.

Most people with atrial or ventricular premature beats have a normal underlying rhythm. The premature beats generally occur within a shorter fixed interval after a normal beat and are followed by an interval which is generally longer that the normal sinus interval. The method of FIG. 1 determines if the premature beats meet these criteria. As step 110 shows, the shortest interval $I_s$ of the N samples and the interval immediately succeeding the interval $I_s$, known as $I_{s+1}$, are determined. Then, as step 112 shows, if the interval $I_{s+1}$ is less than or equal to the mean value M, the heart activity is considered irregular. If the interval $I_{s+1}$ is more less than M, then the intervals $I_s$ and $I_{s+1}$ are deleted from the N sample values, as step 116 shows, and an adjusted mean M' and standard deviation SD' are determined from the remaining intervals. As step 118 shows, when the ratio of SD'/M' is less than P, the heart activity is regular, as step 120 shows. If the ratio is greater than or equal to P, then the shortest interval among the remaining intervals, $I_{s2}$, is selected, as shown at step 122. The absolute value of the difference between $I_{s2}$ and $I_s$ is calculated and compared to an empirically determined value in the range of 0.02–0.8 seconds wherein the preferred value is 0.04 seconds, as shown at step 124. If the absolute value of the difference is greater than the value 0.04 seconds, then the heartbeat is irregular, as step 126 shows. Otherwise, as step 128 shows, the shortest interval of the remaining intervals, $I_{s2}$, is redefined as $I_s$, the immediately following interval is defined as $I_{s+1}$ and steps 112, 116, 118, 122 and 124 are repeated.

The process is repeated until all the intervals corresponding to premature beats are eliminated from the sample and whether the heart activity is normal or irregular is determined. For the occasional patient with premature beats after every normal beat, the algorithm will eliminate all the beats and thereby indicate that the rhythm was a regular rhythm and not atrial fibrillation. For such patients, the standard deviation cannot be calculated because less than two intervals remain in the sample, as shown in step 130.

An example, N=16 intervals are recorded, the mean of the N intervals is M=0.87 seconds, and the standard deviation is SD=0.03 seconds. If a threshold value is P=0.07 then 0.03/0.87<0.07, i.e., SD/M<P. Here, SD/M is less than the threshold value, P, and therefore the sample is regular.

Alternatively, if N=16, M=0.87 seconds and SD=0.12, then 0.12/0.87>0.01 or SD/M>P. In this case, the shortest interval of the first fifteen intervals will be selected which, for example, is $I_s$=0.52 seconds. If the interval $I_s$ is immediately followed by an interval $I_{s+1}$=0.70, the value of $I_{s+1}$ is less than the value M and the rhythm is irregular because the premature beat is followed by an interval which is shorter than the normal sinus interval. Alternatively, if the value of $I_{s+1}$=0.90 seconds, $I_{s+1}$ is greater than M, and both $I_{s+1}$ and $I_s$ are removed from the next calculations. A new mean M' and standard deviation SD' are calculated from the remaining 14 intervals. If a new standard deviation, SD', divided by the new mean M' is less than P, so that SD'/M'<P, then the sample is regular. If not, then the next shortest interval $I_{s2}$ is compared to the first shortest interval $I_s$. If the absolute value of the difference between the two values is greater than the range 0.020–0.08 seconds, then the rhythm is irregular. If it is less than or equal to 0.04 seconds, then the interval following the second shortest interval $I_{s2}$, $I_{s2+1}$, is determined. If this value is less than or equal to the original mean M, then the rhythm is irregular. If it is greater than M, then the $I_{s2}$ and $I_{s2+1}$ values are removed from the samples, and a new mean and new standard: deviation is calculated from the remaining 12 intervals. The process is iterated until the rhythm is determined to be irregular, is determined to be regular or until only one interval remains. In the latter case the rhythm is determined to be regular..

Figure 2:
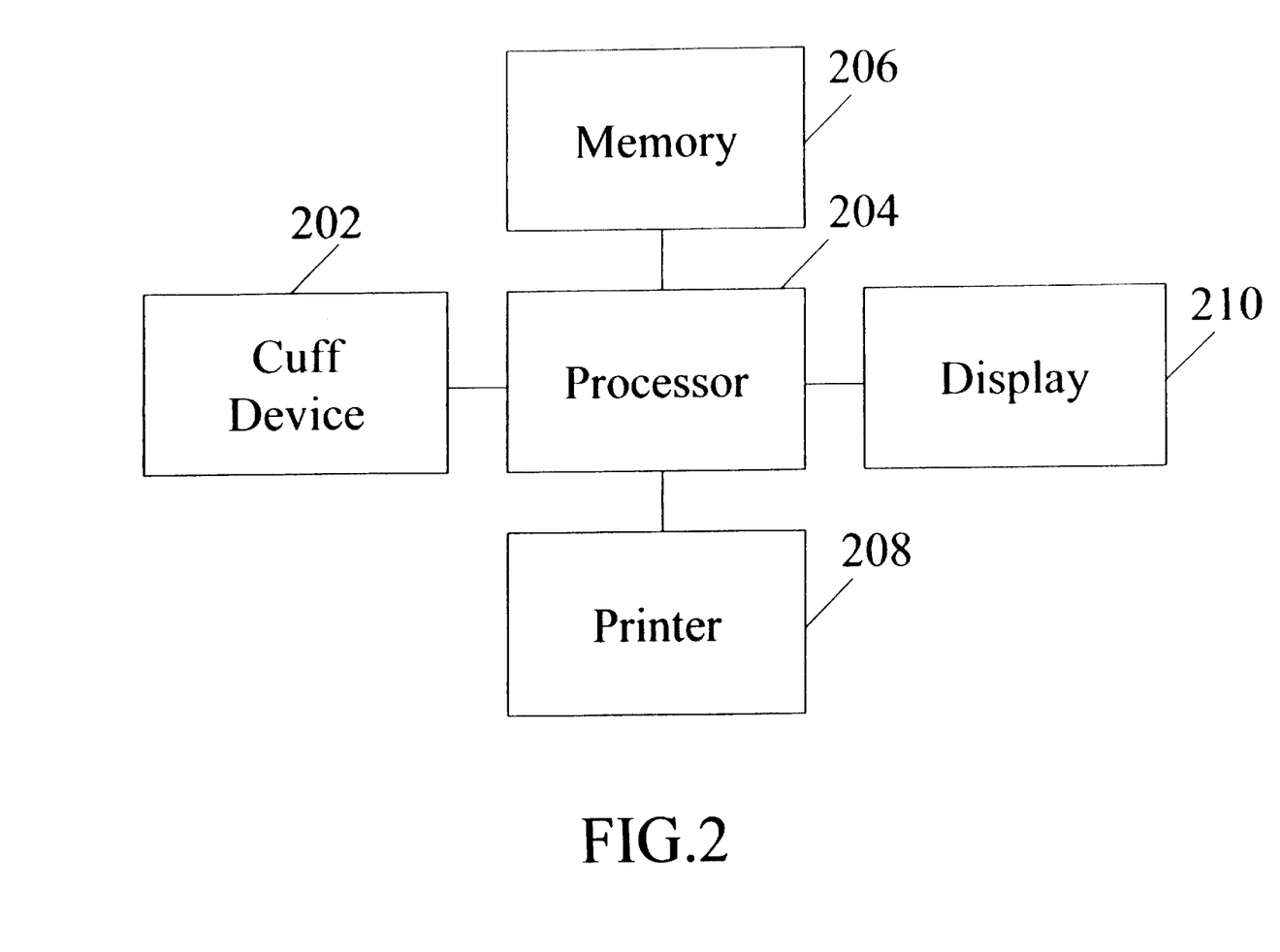
FIG. 2 is a diagram showing an arrangement for detecting possible atrial fibrillation using an inflated cuff in accordance with the invention.
Figure 3:
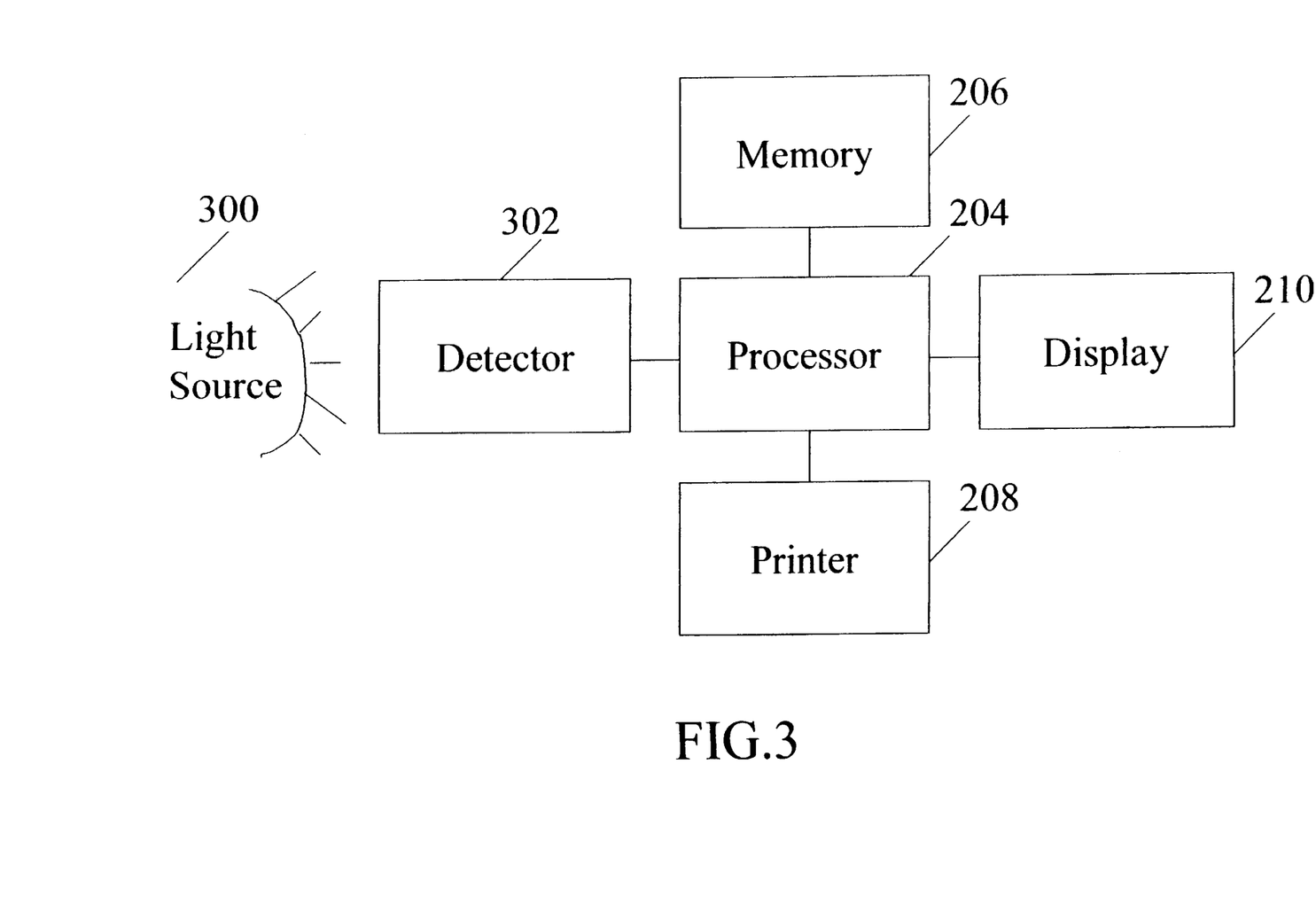
FIG. 3 is a diagram showing an arrangement for detecting possible atrial fibrillation by detecting changes in the amount of blood that is absorbed in an appendage area in accordance with the invention.
Figure 4:
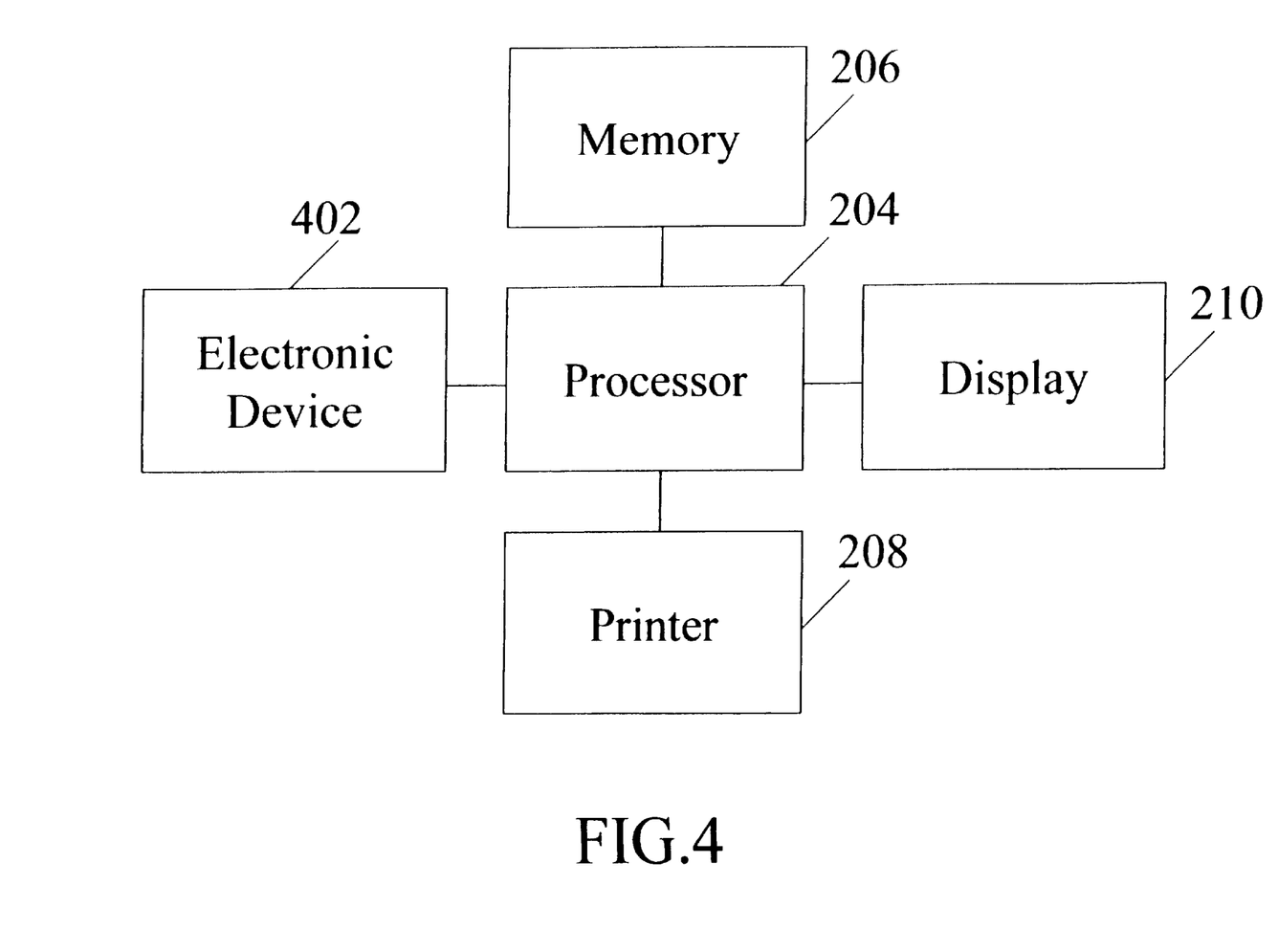
FIG. 4 is a diagram showing an arrangement detecting possible atrial fibrillation using electrodes placed on the skin of an individual in accordance with the invention.

FIGS. 2, 3 and 4 illustrate arrangements which carry out the method of the invention.

FIG. 2 shows an embodiment of the invention in which heartbeat irregularities and possible atrial fibrillation are detected using an inflated-cuff device 202. The inflated-cuff device may be a known apparatus which monitors pulse rates by tracking the systolic peak that coincides with a heartbeat. An inflatable cuff is wrapped around the upper arm of an individual and is inflated to a pressure that is greater than the individual's blood pressure. Each heartbeat creates a rise in the individual's blood pressure which corresponds to a pulse beat. The time of each pulse beat is delivered to a processor 204 which includes instructions that carry out the method shown in FIG. 1. Further, the processor 204 stores the time of each pulse beat, the intervals between pulse beats, and other information in a memory 206. The memory 206 may include RAM or other device memory or include a hard disk, a floppy disk or other memory devices. The processor 204 may comprise a microprocessor, and applications specific integrated circuit (ASIC), a programmable logic array (PLA) or reduced instruction set chip (RISC).

The processor 204 carries out the steps shown in FIG. 1 until it is determined that the heartbeat is regular or irregular. The processor then delivers the results to a printer 208 a display 210 a vibration generator, and/or an auditory generator, etc. which may include an indication that the heartbeat is regular, irregular, in possible atrial fibrillation, or that a physician should be contacted. Other information, such as the heart rate or pulse rate, may also be displayed.

FIG. 3 shows another embodiment of the invention in which the pulse rate is monitored through changes in light transmitted through a body appendage, such as a finger. Light is transmitted by a light source 300 through the finger, or other appendage of an individual, and is received by a detector 302 which measures the change in light transmitted through the appendage to detect a pulse beat. The detector 302 may comprise a known pulse measurement device. The detector 302 delivers the time of each measured pulse to the processor 204 which carries out the operations described above regarding FIG. 2.

FIG. 4 shows a further embodiment of the invention in which actual heartbeats are measured using an electrode device 402 in which electrodes are placed on various locations of an individual. The electrodes may include wrist straps that are placed on the arms or other contacts which are removably secured to various areas on the individual including the torso, arms and legs. The electrode device 402, which may operate in a manner similar to a known EKG device, delivers the time of each measured heartbeat to the processor 204. The processor 204 then carries out the operations described above.

Advantageously, the invention provides a method and apparatus that easily detect the presence of irregular heartbeats from a plurality of heartbeats, pulses or other measurements.

As a further advantage, the invention differentiates normal heart activity from irregular heart activity.

A still further advantage is that the invention provides relatively simple, non-invasive home monitoring.

Although the present invention has been described in relation to particular embodiments thereof, many other variations and modifications and other uses may become apparent to those skilled in the art. It is preferred, therefore, that the present invention be limited not by this specific disclosure herein, but only by the appended claims.

What is claimed is:

1. A method of detecting irregular cardiac activity, said method comprising the steps of:
   (a) determining a plurality of time intervals each corresponding to a respective time period between successive ones of a sequence of heartbeats;
   (b) determining a mean and a standard deviation of said plurality of time intervals;
   (c) selecting, when a quotient formed by dividing said standard deviation by said mean has a value greater than or equal to a threshold value, a shortest one of said plurality of time intervals and a succeeding time interval that immediately follows said shortest one; and
   (d) determining, when said succeeding time interval has a value less than or equal to said mean, that said cardiac activity is irregular.

2. A method of detecting irregular cardiac activity, said method comprising the steps of:
  (a) determining a plurality of time intervals each corresponding to a respective time period between successive ones of a sequence of heartbeats;
  (b) determining a mean and a standard deviation of said plurality of time intervals;
  (c) selecting, when a quotient formed by dividing said standard deviation by said mean has a value greater than or equal to a threshold value, a shortest one of said plurality of time intervals and a succeeding time interval that immediately follows said shortest one;
  (d) deleting, when said succeeding time interval has a value greater than said mean, said shortest one of said plurality of time intervals and said succeeding time interval from said plurality of time intervals;
  (e) determining an adjusted mean and an adjusted standard deviation based on remaining ones of said plurality of time intervals;
  (f) selecting, when an adjusted quotient formed by dividing said adjusted standard deviation by said adjusted mean is greater than or equal to said threshold value, an adjusted shortest one of said remaining ones of said plurality of time intervals; and
  (g) determining, when an absolute value of the difference between said adjusted shortest one and said shortest one is greater than a value within a preselected range between 0.02–0.8 seconds, that said cardiac activity is irregular.

3. A method of detecting irregular cardiac activity, said method comprising the steps of:
  (a) determining a plurality of time intervals each corresponding to a respective time period between successive ones of a sequence of heartbeats;
  (b) determining a mean and a standard deviation of said plurality of time intervals;
  (c) selecting, when a quotient formed by dividing said standard deviation by said mean has a value greater than or equal to a threshold value, a shortest one of said plurality of time intervals and a succeeding time interval that immediately follows said shortest one;
  (d) deleting, when said succeeding time interval has a value greater than said mean, said shortest one of said plurality of time intervals and said succeeding time interval from said plurality of time intervals;
  (e) determining an adjusted mean and an adjusted standard deviation based on remaining ones of said plurality of time intervals;
  (f) selecting, when an adjusted quotient formed by dividing said adjusted standard deviation by said adjusted mean is greater than or equal to said threshold value, an adjusted shortest one of said remaining ones of said plurality of time intervals;
  (g) redefining, when an absolute value of the difference between said adjusted shortest one and said shortest one is less than or equal to a value within a preselected range between 0.02–0.08 seconds, the value of said shortest one of said plurality to be that of said adjusted shortest one and the value of said succeeding one to be that of an interval immediately following said adjusted shortest one; and
  (h) repeating steps (d) through (h) until either said absolute value of a difference between said adjusted shortest one and said shortest one is greater than said value within said preselected range, in which case said cardiac activity is irregular, or until said plurality of time intervals has less than two values, in which case said cardiac activity is regular.

4. The method of claim 1 wherein said sequence of heartbeats is derived from taking a sequence of pulse rates.

5. The method of claim 2 wherein said sequence of heartbeats is derived from taking a sequence of pulse rates.

6. The method of claim 3 wherein said sequence of heartbeats is derived from taking a sequence of pulse rates.

7. The method of claim 1 further comprising the step of storing at least one of said plurality of time intervals, said mean, said standard deviation, said quotient and said threshold value.

8. The method of claim 2 further comprising the step of storing at least one of said plurality of time intervals, said mean, said standard deviation, said quotient and said threshold value.

9. The method of claim 3 further comprising the step of storing at least one of said plurality of time intervals, said mean, said standard deviation, said quotient and said threshold value.

10. The method of claim 1 wherein said sequence of heartbeats is determined by measuring a sequence of heartbeats.

11. The method of claim 2 wherein said sequence of heartbeats is determined by measuring a sequence of heartbeats.

12. The method of claim 3 wherein said sequence of heartbeats is determined by measuring a sequence of heartbeats.

13. An apparatus for detecting irregular cardiac activity, said apparatus comprising:
  a detector for detecting an activity related to heartbeats at measured times;
  a processor for determining whether said measured heart activity is regular or irregular as a function of at least one of a standard deviation and mean of a plurality of time intervals of said heart activity, and a shortest one of said plurality of time intervals, a time interval immediately succeeding said shortest one, and next shortest time interval; and
  a device for outputting an indication whether the activity is regular or irregular.

14. The apparatus of claim 13 wherein said device is an inflatable-cuff device and said activity is a pulse beat.

15. The apparatus of claim 13 wherein said device detect changes in light transmitted through an appendage of an individual and the activity is a pulse rate.

16. The apparatus of claim 13 wherein said detector is an electrode device and the measured activity is an actual heart rate.

17. The apparatus of claim 13 wherein said output device is a printer.

18. The apparatus of claim 13 wherein said device for outputting is a display.

19. The apparatus of claim 13 wherein said device for outputting is an auditory signal generator.

20. The apparatus of claim 13 wherein said device for outputting is a vibration signal generator.

21. The apparatus of claim 13 further comprising a memory device.

22. The apparatus of claim 13 wherein said processor comprises at least one of a microprocessor, an application specific integrated circuit (ASIC), a programmable logic array (PLA) and a reduced instruction set chip (RISC).

23. The apparatus of claim 13 wherein said processor verifies normal cardiac activity by carrying out the steps of:

(a) determining a plurality of time intervals each corresponding to a respective time period between successive ones of a sequence of heartbeats;

(b) determining a mean and a standard deviation of said plurality of time intervals; and (c) determining, when a quotient formed by dividing said standard deviation by said mean is less than a threshold value, that the cardiac activity is regular.

24. The apparatus of claim 13 wherein said processor determines irregular cardiac activity by carrying out the steps of:

(a) determining a plurality of time intervals each corresponding to a respective time period between successive ones of a sequence of heartbeats;

(b) determining a mean and a standard deviation of said plurality of time intervals;

(c) selecting, when a quotient formed by dividing said standard deviation by said mean has a value greater than or equal to a threshold value, a shortest one of said plurality of time intervals and a succeeding time interval that immediately follows said shortest one; and (d) determining, when said succeeding time interval has a value less than or equal to said mean, that said cardiac activity is irregular.

25. The apparatus of claim 13 wherein said processor detects irregular cardiac activity by carrying out the steps of:

(a) determining a plurality of time intervals each corresponding to a respective time period between successive ones of a sequence of heartbeats;

(b) determining a mean and a standard deviation of said plurality of time intervals;

(c) selecting, when a quotient formed by dividing said standard deviation by said mean has a value greater than or equal to a threshold value, a shortest one of said plurality of time intervals and a succeeding time interval that immediately follows said shortest one;

(d) deleting, when said succeeding time interval has a value greater than said mean, said shortest one of said plurality of time intervals and said succeeding time interval from said plurality of time intervals;

(e) determining an adjusted mean and an adjusted standard deviation based on remaining ones of said plurality of time intervals;

(f) selecting, when an adjusted quotient formed by dividing said adjusted standard deviation by said adjusted mean is greater than or equal to said threshold value, an adjusted shortest one of said remaining ones of said plurality of time intervals; and (g) determining, when an absolute value of the difference between said adjusted shortest one and said shortest one is greater than a value within a preselected range between 0.02–0.008, seconds that said cardiac activity is irregular.

26. The apparatus of claim 13 wherein said processor determines irregular cardiac activity by carrying out the steps of:

(a) determining a plurality of time intervals each corresponding to a respective time period between successive ones of a sequence of heartbeats;

(b) determining a mean and a standard deviation of said plurality of time intervals;

(c) selecting, when a quotient formed by dividing said standard deviation by said mean has a value greater than or equal to a threshold value, a shortest one of said plurality of time intervals and a succeeding time interval that immediately follows said shortest one;

(d) deleting, when said succeeding time interval has a value greater than said mean, said shortest one of said plurality of time intervals and said succeeding time interval from said plurality of time intervals (e) determining an adjusted mean and an adjusted standard deviation based on remaining ones of said plurality of time intervals;

(f) selecting, when an adjusted quotient formed by dividing said adjusted standard deviation by said adjusted mean is greater than or equal to said threshold value, an adjusted shortest one of said remaining ones of said plurality of time intervals;

(g) redefining, when an absolute value of the difference between said adjusted shortest one and said shortest one is less than or equal a value within a preselected range between 0.02–0.08 seconds, the value of said shortest one of said plurality to be that of said adjusted shortest one and the value of said succeeding one to be that of an interval immediately following said adjusted shortest one; and (h) repeating steps (d) through (h) until either an absolute value of a difference between said adjusted shortest one and said shortest one is greater than said value within said preselected range, in which case said cardiac activity is irregular, or until said plurality of time intervals has less than two values, in which case said cardiac activity is regular.

27. The method of claim 1 wherein said threshold value is within the range of 0.05 to 0.10.

28. The method of claim 2 wherein said threshold value is within the range of 0.05 to 0.10.

29. The method of claim 3 wherein said threshold value is within the range of 0.05 to 0.10.

30. The apparatus of claim 23 wherein said threshold value is within the range of 0.05 to 0.10.

31. The apparatus of claim 24 wherein said threshold value is within the range of 0.05 to 0.10.

32. The apparatus of claim 25 wherein said threshold value is within the range of 0.05 to 0.10.

33. The apparatus of claim 26 wherein said threshold value is within the range of 0.05 to 0.10.

34. A method verifying regular cardiac activity, said method comprising the steps of:

(a) determining a plurality of time intervals each corresponding to a respective time period successive ones of a sequence of heartbeats;

(b) determining a mean and a standard deviation of said plurality of time intervals;

(c) selecting, when a quotient formed by dividing said standard deviation by said mean has a value greater than or equal to a threshold value, a shortest one of said plurality of time intervals and a succeeding time interval that immediately follows said shortest one;

(d) deleting, when said succeeding time has a value greater than said mean, said shortest one of said plurality of time intervals and said succeeding time interval from said plurality of time intervals;

(e) determining an adjusted mean and an adjusted standard deviation based on remaining ones of said plurality of time intervals; and (f) determining, when an adjusted quotient formed by dividing said adjusted standard deviation by said adjusted mean is less than said threshold value, that said cardiac activity is regular.

35. The method of claim 34 wherein said sequence of heartbeats is derived from taking a sequence of pulse rates.

36. The method of claim 34 further comprising the step of storing at least one of said plurality of time intervals, said mean, said standard deviation, said quotient and said threshold value.

37. The method of claim 34 wherein said sequence of heartbeats is determined by measuring a sequence of heartbeats.

38. The method of claim 34 wherein said threshold value is within the range 5% to 10%.

39. The apparatus of claim 13 wherein said processor verifies regular cardiac activity by carrying out the steps of:
 (a) determining the plurality of time intervals each corresponding to a respective time period between successive ones of a sequence of heartbeats;
 (b) determining a standard deviation and mean of said plurality of time intervals;
 (c) selecting, when a quotient formed by dividing said standard deviation by said mean has a value greater than or equal to a threshold value, a shortest one of said plurality of time intervals and a succeeding time interval that immediately follows said shortest one;
 (d) deleting, when said succeeding time has a value greater than said mean, said shortest one of said plurality of time intervals and said succeeding time interval from said plurality of time Intervals;
 (e) determining an adjusted mean and an adjusted standard deviation based on remaining ones of said plurality of time intervals; and
 (f) determining, when an adjusted quotient formed by dividing said adjusted standard deviation by said adjusted mean is less than said threshold value, that said cardiac activity is regular.

40. A method of detecting irregular cardiac activity, said method comprising the steps of:
 (a) determining a plurality of time intervals each corresponding to a respective time period between successive ones of sequence of heartbeats;
 (b) determining a mean and a standard deviation of said plurality of time intervals;
 (c) selecting when a quotient formed by dividing said standard deviation by said mean has a value greater than or equal to a threshold value, a shortest one of said plurality of time intervals and a succeeding time interval that immediately follows said shortest one;
 (d) deleting, when said succeeding time interval has a value greater than said mean, said shortest one of said plurality of time intervals and said succeeding time interval from said plurality of time intervals;
 (e) determining an adjusted mean and an adjusted standard deviation based on remaining ones of said plurality of time intervals; and
 (f) determining, when an adjusted quotient formed by dividing said adjusted standard deviation with said adjusted mean is less than a threshold value, that said cardiac activity tis irregular.

* * * * *